US012593956B2

(12) United States Patent
Yangdai

(10) Patent No.: US 12,593,956 B2
(45) Date of Patent: Apr. 7, 2026

(54) METHOD FOR BUILDING IMAGE READING MODEL BASED ON CAPSULE ENDOSCOPE, DEVICE, AND MEDIUM

(71) Applicants: ANKON TECHNOLOGIES CO., LTD, Wuhan (CN); ANX IP HOLDING PTE. LTD., Singapore (SG)

(72) Inventor: Tianyi Yangdai, Wuhan (CN)

(73) Assignees: ANKON TECHNOLOGIES CO., LTD, Wuhan (CN); ANX IP HOLDING PTE. LTD., Singapore (SG)

( * ) Notice: Subject to any disclaimer, the term of this patent is extended or adjusted under 35 U.S.C. 154(b) by 179 days.

(21) Appl. No.: 18/551,297

(22) PCT Filed: Mar. 15, 2022

(86) PCT No.: PCT/CN2022/080840
§ 371 (c)(1),
(2) Date: Sep. 19, 2023

(87) PCT Pub. No.: WO2022/194126
PCT Pub. Date: Sep. 22, 2022

(65) Prior Publication Data
US 2024/0188791 A1 Jun. 13, 2024

(30) Foreign Application Priority Data
Mar. 19, 2021 (CN) .......................... 202110296737.2

(51) Int. Cl.
*A61B 1/00* (2006.01)
*A61B 1/04* (2006.01)
(Continued)

(52) U.S. Cl.
CPC .......... *A61B 1/00009* (2013.01); *A61B 1/041* (2013.01); *A61B 1/045* (2013.01);
(Continued)

(58) Field of Classification Search
CPC ..... A61B 1/00009; A61B 1/041; A61B 1/045; A61B 1/000094; A61B 1/000096;
(Continued)

(56) References Cited

U.S. PATENT DOCUMENTS 10,314,514 B2 * 6/2019 Duan ...................... A61B 5/067
2005/0054897 A1 * 3/2005 Hashimoto .......... A61B 5/0031
600/118
(Continued)

FOREIGN PATENT DOCUMENTS

CN 103300862 A 9/2013
CN 105942959 A 9/2016
(Continued)

*Primary Examiner* — Sheree N Brown
(74) *Attorney, Agent, or Firm* — Treasure IP Group, LLC

(57) ABSTRACT

The present invention provides a method for building an image reading model based on a capsule endoscope, a device and a medium. The method includes: driving the capsule endoscope to move within a working area, sequentially recording position coordinates and field of view orientations of the capsule endoscope when it reaches each positioning point at a predetermined first frequency, and driving the capsule endoscope to sequentially capture and record images at a predetermined second frequency; constructing a 3D model corresponding to the outer contour of the working area based on the recorded position coordinates of the capsule endoscope at each positioning point; and mapping the recorded images onto the 3D model to create an image reading model. By mapping the obtained images onto a 3D model of the working area, to enhance the visualization (Continued)

S1
Drive a capsule endoscope to move within a working area, sequentially record the position coordinates and field of view orientations of the capsule endoscope when it reaches each positioning point at a predetermined first frequency, and drive the capsule endoscope to sequentially capture images at a predetermined second frequency and record the images S2
construct a 3D model corresponding to the outer contour of the working area based on the recorded position coordinates of the capsule endoscope at each positioning point S3
map the recorded images onto the 3D model to create an image reading model effect of the examination, facilitate observation, save image reading time, and increase the detection efficiency.

8 Claims, 3 Drawing Sheets

(51) Int. Cl.

| | |
|---|---|
| *A61B 1/045* | (2006.01) |
| *G06T 7/00* | (2017.01) |
| *G06T 7/11* | (2017.01) |
| *G06T 7/73* | (2017.01) |
| *G06T 15/06* | (2011.01) |
| *G06T 17/00* | (2006.01) |
| *G06V 10/764* | (2022.01) |
| *G06V 20/70* | (2022.01) |

(52) U.S. Cl.
CPC .............. *G06T 7/0014* (2013.01); *G06T 7/11* (2017.01); *G06T 7/75* (2017.01); *G06T 15/06* (2013.01); *G06T 17/00* (2013.01); *G06T 2207/20021* (2013.01); *G06T 2207/30092* (2013.01); *G06T 2207/30168* (2013.01); *G06T 2210/21* (2013.01); *G06T 2210/41* (2013.01); *G06T 2210/56* (2013.01); *G06V 10/764* (2022.01); *G06V 20/70* (2022.01)

(58) Field of Classification Search
CPC ..... A61B 1/00194; G06T 7/0014; G06T 7/11; G06T 7/75; G06T 15/06; G06T 17/00; G06T 2207/20021; G06T 2207/30092; G06T 2207/30168; G06T 2210/21; G06T 2210/41; G06T 2210/56; G06T 5/20; G06T 19/20; G06T 2200/08; G06T 2207/10068; G06V 10/764; G06V 20/70; G16H 30/00
USPC ........................................................ 345/419
See application file for complete search history.

(56) References Cited

U.S. PATENT DOCUMENTS

| | | | |
|---|---|---|---|
| 2007/0002038 A1* | 1/2007 | Suzuki ................... | A61B 5/065 |
| | | | 345/419 |
| 2008/0199100 A1* | 8/2008 | Ishiga ....................... | G06T 5/20 |
| | | | 382/263 |
| 2010/0119110 A1* | 5/2010 | Kanda ..................... | G06F 18/21 |
| | | | 382/128 |
| 2017/0046833 A1* | 2/2017 | Lurie ...................... | G06T 17/20 |
| 2018/0308235 A1* | 10/2018 | Yuan ......................... | G06T 7/70 |
| 2021/0195102 A1* | 6/2021 | Yangdai ............. | A61B 1/00006 |

FOREIGN PATENT DOCUMENTS

| | | | |
|---|---|---|---|
| CN | 106934799 A | | 7/2017 |
| CN | 108430373 A | | 8/2018 |
| CN | 111932532 A | | 11/2020 |
| CN | 112089392 A | | 12/2020 |
| CN | 112842320 A | | 5/2021 |
| CN | 119943339 A | * | 5/2025 |
| JP | 2017108971 A | | 6/2017 |

* cited by examiner

S1

Drive a capsule endoscope to move within a working area, sequentially record the position coordinates and field of view orientations of the capsule endoscope when it reaches each positioning point at a predetermined first frequency, and drive the capsule endoscope to sequentially capture images at a predetermined second frequency and record the images

S2 construct a 3D model corresponding to the outer contour of the working area based on the recorded position coordinates of the capsule endoscope at each positioning point

S3 map the recorded images onto the 3D model to create an image reading model

FIG. 1

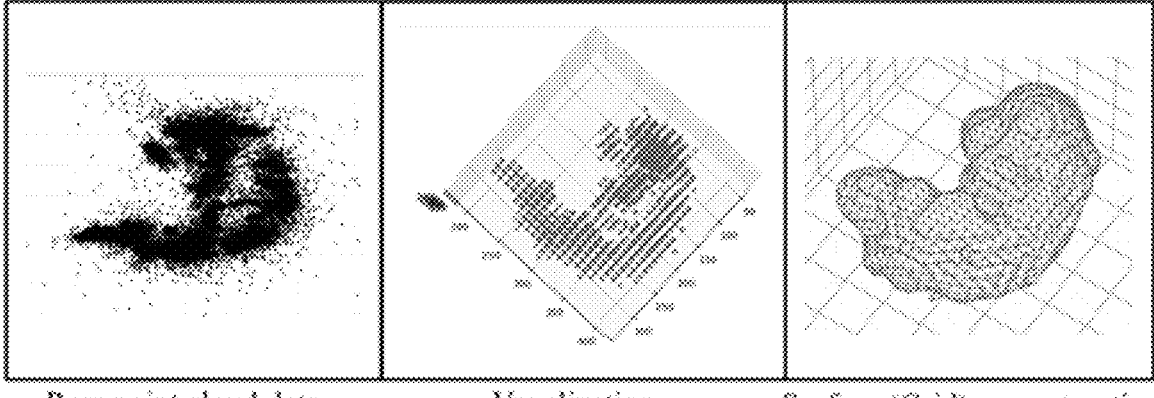

Raw point cloud data          Voxelization          Surface (Grid) reconstruction

FIG. 2

METHOD FOR BUILDING IMAGE READING MODEL BASED ON CAPSULE ENDOSCOPE, DEVICE, AND MEDIUM

CROSS-REFERENCE OF RELATED APPLICATIONS

The application claims priority from Chinese Patent Application No. 202110296737.2, filed Mar. 19, 2021, entitled "Method for Building Image Reading Model Based on Capsule Endoscope, Device, and Medium", all of which are incorporated herein by reference in their entirety.

FIELD OF INVENTION

The present invention relates to the field of medical devices, and more particularly to a method for building an image reading model based on a capsule endoscope, an electronic device, and a readable storage medium.

BACKGROUND

Capsule endoscopes are increasingly used for gastrointestinal examinations. A capsule endoscope is ingested and passes through the oral cavity, esophagus, stomach, small intestine, large intestine, and is ultimately expelled from the body. Typically, the capsule endoscope moves passively along with gastrointestinal peristalsis, capturing images at a certain frame rate during this process. The images are then used by a physician to assess the health condition of various regions of a patient's gastrointestinal tract.

Taking an example of gastric examinations using a capsule endoscope, the position and orientation of the capsule endoscope can be adjusted under the control of an external magnetic system to conduct a more thorough examination of the stomach. The usual duration for a gastric examination is 10 to 20 minutes, resulting in approximately 2400 to 4800 images when captured at a frame rate of 4 frames per second (fps). After the examination, these image data are uploaded for medical professional reference. Usually, medical professionals review the uploaded image data in a passive manner. They can only observe the images in the order they were captured or select them using a progress bar. This approach lacks the spatial context that relates the images to the actual structures within the digestive tract. Medical professionals need to rely on their own deduction and spatial reconstruction to interpret the images. This process can introduce interference in terms of image understanding and assessing the completeness of the examination, especially for less experienced examiners who may find it challenging to review the image data displayed in this manner.

SUMMARY OF THE INVENTION

In order to solve the above technical problems in the prior art, it is an object of the present invention to provide a method for building an image reading model based on a capsule endoscope, an electronic device, and a readable storage medium.

In order to achieve one of the above objects of the present invention, one embodiment of the present invention provides a method for building an image reading model based on a capsule endoscope. The method comprises: driving the capsule endoscope to move within a working area, sequentially recording position coordinates and field of view orientations of the capsule endoscope when it reaches each positioning point at a predetermined first frequency, and driving the capsule endoscope to sequentially capture images at a predetermined second frequency and record the images;

constructing a 3D model corresponding to the outer contour of the working area based on the recorded position coordinates of the capsule endoscope at each positioning point;

mapping the recorded images onto the 3D model to create the image reading model.

In an embodiment of the present invention, the step "constructing a 3D model corresponding to the outer contour of the working area based on the recorded position coordinates of the capsule endoscope at each positioning point" comprises:

obtaining all position coordinates of the capsule endoscope to form a raw point cloud data;

generating a 3D model corresponding to the outer contour of the working area after applying Gaussian filtering, voxelization, voxel shell extraction, smoothing filtering, and surface reconstruction sequentially to the raw point cloud data; where the 3D model is represented by $\Omega(p)$, $$\Omega(p) = \begin{cases} 1, & p \text{ is on the outer contour of the working area} \\ 0, & p \text{ is inside or outside the circle of the outer} \\ & \text{contour of the working area} \end{cases}$$

In an embodiment of the present invention, the step "mapping the recorded images onto the 3D model to create an image reading model" comprises:

dividing the 3D model into a plurality of sub-areas according to the structure of the working area;

mapping the recorded images to each sub-area to create a set of sub-area images, with each image mapped to a unique sub-area;

merging the set of the sub-area images on the 3D model to form the image reading model.

In an embodiment of the present invention, the step "mapping the recorded images to each sub-area to create a set of sub-area images" comprises:

iterating through each image and obtaining the positioning point with the closest capture time to the current image;

planning a virtual ray using the position coordinates of the obtained positioning point as a starting point and the corresponding field of view orientation as an extending direction, and obtaining an intersection point between the virtual ray and the 3D model;

obtaining the sub-area to which the position coordinates of current intersection point belong, and mapping the current image to the sub-area to which the position coordinates of current intersection point belong to form the set of the sub-area images.

In an embodiment of the present invention, the method further comprises: setting the first frequency to be higher than the second frequency.

In an embodiment of the present invention, applying an interpolation filtering over a time sequence to supplement missing positioning points based on the existing positioning points.

In an embodiment of the present invention, after assigning all images to their respective sets of sub-area images, the method further comprises: constructing a cross-verification set;

verifying the images in the each set of the sub-area images, and/or verifying the quality of the images in each set of the sub-area images; where if an image does not belong to its current set, and/or if an image quality score of the image is below a preset value, moving the current image to the cross-verification set.

In an embodiment of the present invention, after assigning all images to their respective sets of the sub-area images, the method further comprises:

identifying and labeling the attribute for each image in each set of the sub-area images;

grouping the images with similar labels in each set of the sub-area images into one group;

generating a mapping identifier separately for each group of images with similar labels on the image reading model.

In order to achieve one of the above objects of the present invention, one embodiment of the present invention provides an electronic device, comprising a memory and a processor. The memory stores a computer program that can run on the processor, and the processor executes the program to implement the steps of the method for building an image reading model based on a capsule endoscope.

In order to achieve one of the above objects of the present invention, one embodiment of the present invention provides a computer-readable storage medium for storing a computer program. The computer program is executed by the processor to implement the steps of the method for building an image reading model based on a capsule endoscope.

The present invention has the following advantages compared with the prior art. The present invention provides the method for building the image reading model based on the capsule endoscope, the electronic device, and the readable storage medium, which can, by mapping the obtained images onto a 3D model of the working area, to enhance the visualization effect of the examination, facilitate observation, save image reading time, and increase the detection efficiency.

BRIEF DESCRIPTION OF THE DRAWINGS

FIG. 1 is an exemplar process flow diagram of a method for building an image reading model based on a capsule endoscope, in accordance with an embodiment of the present invention.

FIG. 2 is a structural schematic diagram of a specific example of the present invention.

DETAILED DESCRIPTION

Figure 3:
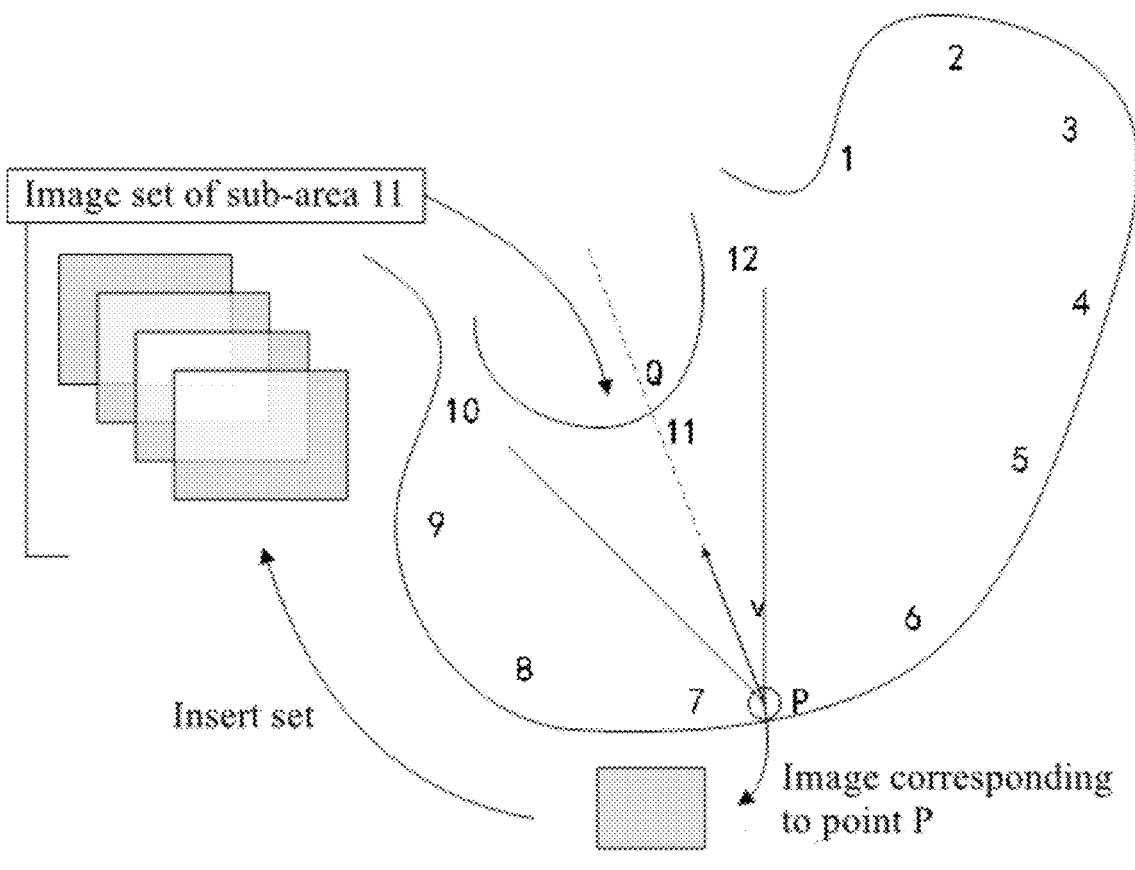
FIG. 3 is a structural schematic diagram of a sub-area in a specific example of the present invention.

The present invention can be described in detail below with reference to the accompanying drawings and preferred embodiments. However, the embodiments are not intended to limit the invention, and the structural, method, or functional changes made by those skilled in the art in accordance with the embodiments are included in the scope of the present invention.

Referring to FIG. 1, in a first embodiment, the present invention provides a method for building an image reading model based on a capsule endoscope. The method comprises the following steps:

step S1, driving the capsule endoscope to move within a working area, sequentially recording position coordinates and field of view orientations of the capsule endoscope when it reaches each positioning point at a predetermined first frequency, and driving the capsule endoscope to sequentially capture images at a predetermined second frequency and record the images;

step S2, constructing a 3D model corresponding to the outer contour of the working area based on the recorded position coordinates of the capsule endoscope at each positioning point;

step S3, mapping the recorded images onto the 3D model to create an image reading model.

After the capsule endoscope moves into the working area, it records each working point at a predetermined frequency, and depending on specific requirements, it records the spatial coordinate value P(x, y, z), and the field of view orientation V of each working point. The field of view orientation here refers to the orientation of the capsule endoscope, which may be Euler angles (yaw, pitch, roll) for example, or quaternions, or vector coordinates of the orientation. Based on the field of view orientation, it can determine the field of view of the capsule endoscope capturing image in the orientation V at the current coordinate point. The field of view forms a conical shape with the current coordinate point as a starting point, of which, the vector direction is $\overrightarrow{PV}$, that is the extension of the axis of the cone. Capturing images with the capsule endoscope, orienting its positioning coordinates, and recording the field of view orientation are all established techniques in the prior art.

For example, the present invention extends to the content of Chinese patent application 201911188050.6, entitled "Positioning system and method for swallowable device", which describes a system and method for locating a swallowable device, such as a capsule endoscope, to obtain its position coordinates and field of view orientation, and without further elaboration here.

For step S2, as illustrated in FIG. 2, after completing step S1, in a three-dimensional spatial coordinate system, the position coordinates of each capsule endoscope at various positioning points within the working area form a raw point cloud data. Accordingly, the step S2 specifically comprises:

obtaining all position coordinates of the capsule endoscope to form the raw point cloud data;

after applying Gaussian filtering, voxelization, voxel shell extraction, smoothing filtering, and surface reconstruction sequentially to the raw point cloud data to generate a 3D model corresponding to the outer contour of the working area.

The 3D model is represented by $\Omega(p)$, $$\Omega(p) = \begin{cases} 1, & p \text{ is on the outer contour of the working area} \\ 0, & p \text{ is inside or outside the circle of the outer} \\ & \text{contour of the working area} \end{cases}.$$

In this specific example, taking the working area as the stomach space as an example, the capsule endoscope, while operating within the working area, may float in the fluid inside the stomach, remain attached to the inner wall, rotating, or flipping. This may result in obtaining a very dense point cloud, as shown in the leftmost image in FIG. 2.

Further, the raw point cloud data is often extensive and relatively noisy. However, after undergoing Gaussian filtering and voxelization, the resulting data can make the contour of the working area clearer. In this context, the outer contour of the working area typically refers to the maximum external boundary of the working area, as illustrated in the middle image in FIG. 2. Further, after voxelization, the data undergoes voxel shell extraction (edge extraction) to filter out outliers. Further, applying additional smoothing filtering (networking the data) results in a relatively dense surface image, as depicted in the rightmost image in FIG. 2, that is, the 3D model of the outer contour of the working area, as described in the present invention.

In practical applications, the 3D model can be visualized on a computer front-end display interface, and the visual angle of the 3D model can be changed using external input devices such as a mouse, touchscreen, and so on. The reconstructed 3D model only contains the surface data of the working area, that is, as shown in the following formula, the data 2 of the 3D model only contains the surface data of the model, that is the surface data of the working area.

$$\Omega(p) = \begin{cases} 1, & p \text{ is on the outer contour of the working area} \\ 0, & p \text{ is inside or outside the circle of the outer} \\ & \text{contour of the working area} \end{cases}$$

In practical applications, there are various methods to implement the step S2, which means there are a plurality of approaches to process known point cloud data and generate 3D surface models, and without further elaboration here.

Preferably, the step S3 comprises the following steps:

step S31, dividing the 3D model into a plurality of sub-areas according to the structure of the working area;

step S32, mapping the recorded images to each sub-area to create a set of sub-area images, with each image mapped to a unique sub-area;

step S33, merging the set of the sub-area images on the 3D model to form the image reading model.

In the computer front-end display interface, when assisting in selecting a sub-area of the image reading model, it is associated to open the set of the corresponding sub-area images, and selectively open any one of the images corresponding to the current set of the sub-area images.

For step S31, the quantity of the sub-areas may be specifically set as required. In a preferred embodiment of the present invention, since the environment in which the capsule endoscope operates is typically a cavity formed by anatomical structures, it is possible to divide the sub-areas based on the specific classification of anatomical structures. This means that anatomical structures with similar attributes can be grouped together into one sub-area, or anatomical structures with similar attributes can be classified into multiple sub-areas. Preferably, when dividing the sub-areas, it is best to have one sub-area correspond to only one anatomical structure. This allows for a more specific classification, making it easier for the subsequent application of the image reading model.

Referring to FIG. 3, continuing with the example of the stomach cavity as the working area, when dividing it based on anatomical structure attributes, it typically includes finer-grained anatomical structures such as the fundus and greater curvature. In a specific example of the present invention, for step S31, the stomach cavity is divided into 12 sub-areas based on its attributes. The quantity of sub-areas can be more. More sub-areas may result in increased computational load of data. However, more sub-areas provide a finer level of classification, leading to more precise computational results. For example, dividing the stomach cavity into 20 sub-areas based on its attributes. In the examples of the present invention, the stomach cavity is divided into 12 sub-areas based on its attributes. Here, although FIG. 3 is presented in the form of a 2D schematic, in practical applications, it can be a three-dimensional (3D) model. Accordingly, the 12 sub-areas are contiguous in sequence based on the anatomical attributes. For example, sub-area 2 and sub-area 3 have the attribute "Fundus", and sub-area 5 and sub-area 6 have the attribute "Greater Curvature".

Preferably, for step S32, comprising: step S321, matching a time sequence, iterating through each image and obtaining the positioning point with the closest capture time to the current image; step S322, planning a virtual ray using the position coordinates of the obtained positioning point as a starting point and the corresponding field of view orientation as an extending direction, and obtaining an intersection point between the virtual ray and the 3D model; step S323, obtaining the sub-area to which the position coordinates of current intersection point belong, and mapping the current image to the sub-area to which the position coordinates of current intersection point belong to form a set of the sub-area images.

Preferably, for step S321, during the locating process of the position of the capsule endoscope, the number of positioning points may decrease due to environmental factors such as signal interference and motion disturbances. Thus, setting the first frequency higher than the second frequency, that is, the positioning frequency is set to be higher than the image capture frequency. For example, in a specific example of the present invention, the first frequency is set to 40 to 100 Hz, and the second frequency is set to be lower than 30 fps. As a result, it is still possible to obtain more densely spaced positioning results than image capture, thus achieving the effect of matching each image to positioning points with closer acquisition time.

Figure 4:
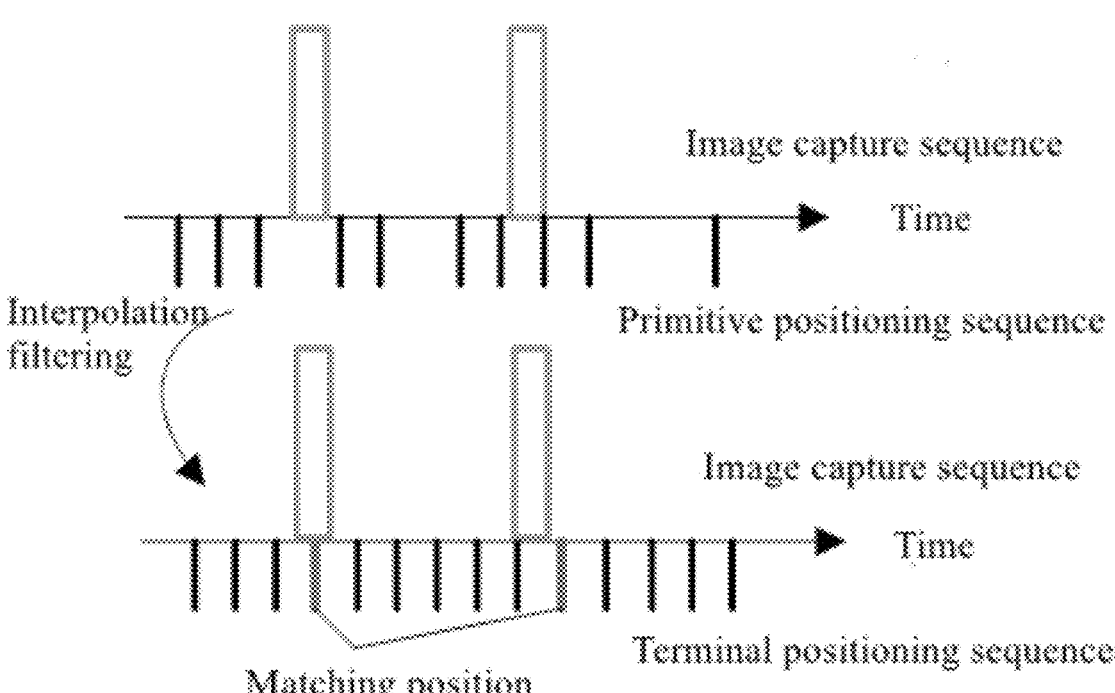
FIG. 4 is a structural schematic diagram of a specific example of matching images with positioning points.

Preferably, as illustrated in FIG. 4, applying an interpolation filtering over the time sequence to supplement missing positioning points based on the existing positioning points. This step ensures a more precise matching of images with positioning points.

Continuing with the example shown in FIG. 3, for step S322, the positioning points that match the images all have corresponding position coordinates and field of view orientations. Taking the current image-matched positioning point P as an example, with P as the coordinate starting point, it is located either on or inside the 3D model $\Omega(p)$. V represents the field of view orientation, which is the extension direction of the ray. Based on this ray, the intersection point Q of the ray extending towards the direction V with the 3D model $\Omega(p)$ when located at point P can be obtained.

Further, in accordance with step S323, based on the area division of the 3D model, the sub-area to which the intersection point Q belongs can be obtained. In this example, point Q belongs to the sub-area 11. At this point, the image corresponding to point P is mapped to the sub-area 11, forming one of the images in the set of the sub-area images for the sub-area 11.

Preferably, between step S32 and step S33, the method further comprises: constructing a cross-verification set; verifying the images in the each set of the sub-area images, and/or verifying the quality of the images in each set of the sub-area images; where if an image does not belong to its current set, and/or if the image quality score is below a preset value, moving the current image to the cross-verification set.

Here, the presence of various errors, such as improper boundary settings for sub-areas, may lead to errors in image attribution set. Furthermore, low-quality images can have a detrimental impact when called upon later. Therefore, cross-verification of the images between step S32 and step S33 is performed to remove any poor-quality data from the various sets of the sub-area images. In the examples of the present invention, there are various methods for image verification. The present invention references to the Chinese patent application CN106934799A, entitled "Auxiliary image reading system and method for capsule endoscope" in its entirety to verify the images in each set of the sub-area images and determine whether they belong to the current set. In addition, the present invention references to the Chinese patent application CN111932532A, entitled "Referenceless image evaluation method for capsule endoscope, electronic device, and medium" in its entirety to verify the quality of the images in each set of the sub-area images and determine whether the image quality is appropriate. The images with inadequate image quality or low-quality scores are transferred to a cross-verification set. The scoring in the present invention may be an image quality evaluation score, and/or an image content evaluation score, and/or a composite score, as mentioned in the cited patent. Further details are not provided here.

It should be noted that, errors may also be present in the process of verifying the images in the each set of the sub-area images, and/or verifying the quality of the images in each set of the sub-area images. Therefore, the cross-verification set is retained, and the data in this cross-verification set can also be selectively accessed or reclassified later, without further elaboration here.

For step S33, the formed image reading model is visualized in the computer front-end display interface. When assisting in selecting a sub-area of the image reading model, it is associated to open the corresponding set of the sub-area images, and selectively open any one of the images corresponding to the current set of the sub-area images.

Preferably, after assigning all images to their respective sets of the sub-area images, the method further comprises: identifying and labeling the attribute for each image in each set of the sub-area images; grouping the images with similar labels in each set of the sub-area images into one group; generating a mapping identifier separately for each group of images with similar labels on the image reading model.

Figure 5:
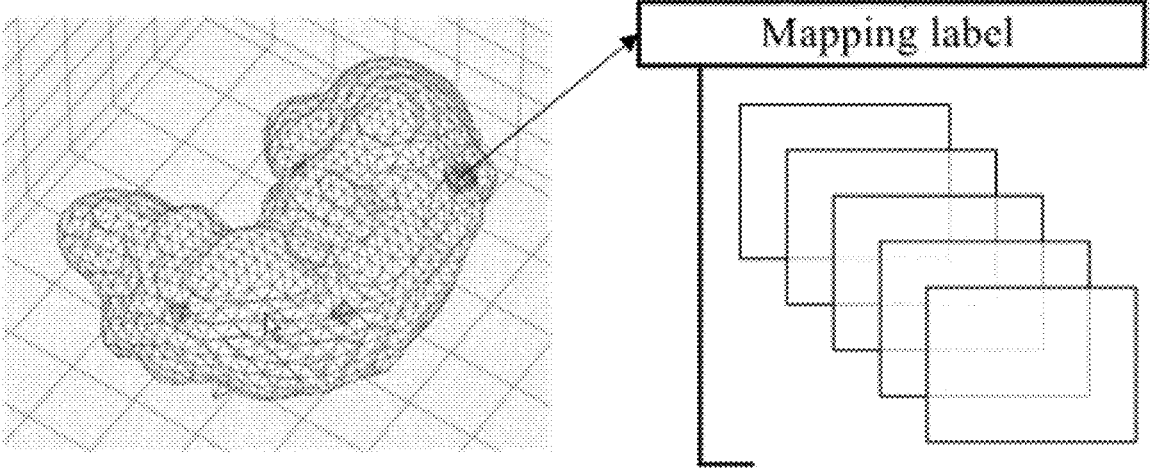
FIG. 5 is a structural schematic diagram of generating mapping an identifier from an image.

Here, as illustrated in FIG. 5, lesions within the images are identified, and their types are specifically labeled. The labeling can be done manually or automatically by an Artificial Intelligence (AI) system. Further, images with the same label are classified into one group, and an additional mapping identifier is generated on the image reading model. When this mapping identifier is selected, the corresponding image can be opened, making it convenient for subsequent centralized search.

Further, one embodiment of the present invention provides an electronic device, comprising a memory and a processor. The memory stores a computer program that can run on the processor, and the processor executes the program to implement the steps of the method for building the image reading model based on the capsule endoscope.

Further, one embodiment of the present invention provides a computer-readable storage medium for storing a computer program. The computer program is executed by the processor to implement the steps of the method for building the image reading model based on the capsule endoscope.

In summary, the present invention provides the method for building the image reading model based on the capsule endoscope, the electronic device, and the readable storage medium, which can, by mapping the obtained images onto a 3D model of the working area, to enhance the visualization effect of the examination, and though various types of mapping, during subsequent use, it becomes convenient to obtain the required images from the simulated image reading model, which enhances interactivity and operability, and facilitates observation, saves images reading time, and improves detection efficiency.

It should be understood that, although the description is described in terms of embodiments, not every embodiment merely comprises an independent technical solution. Those skilled in the art should have the description as a whole, and the technical solutions in each embodiment may also be combined as appropriate to form other embodiments that can be understood by those skilled in the art.

The series of detailed descriptions set forth above are only specific descriptions of feasible embodiments of the present invention and are not intended to limit the scope of protection of the present invention. On the contrary, many modifications and variations are possible within the scope of the appended claims.

The invention claimed is:

1. A method for building an image reading model based on a capsule endoscope, comprising:

driving the capsule endoscope to move within a working area, sequentially recording position coordinates and field of view orientations of the capsule endoscope at each positioning point at a predetermined first frequency, and driving the capsule endoscope to sequentially capture images at a predetermined second frequency and record the images;

constructing a 3D model corresponding to an outline of the working area based on the recorded position coordinates of the capsule endoscope at each location point;

mapping the recorded images onto the 3D model to create the image reading model;

wherein constructing a 3D model corresponding to the outer contour of the working area based on the recorded position coordinates of the capsule endoscope at each positioning point comprises:

obtaining all position coordinates of the capsule endoscope to form a raw point cloud data;

generating a 3D model corresponding to the outer contour of the working area after applying Gaussian filtering, voxelization, voxel shell extraction, smoothing filtering, and surface reconstruction sequentially to the raw point cloud data;

$$\Omega(p) = \begin{cases} 1, & p \text{ is on the outer contour of the working area} \\ 0, & p \text{ is inside or outside the circle of} \\ & \text{the outer contour of the working area} \end{cases}$$

Wherein the 3D model is represented by $\Omega(p)$.

2. The method of claim 1, wherein mapping the recorded images onto the 3D model to create an image reading model comprises:

dividing the 3D model into a plurality of sub-areas according to the structure of the working area;

mapping the recorded images to each sub-area to create a set of sub-area images, with each image mapped to a unique sub-area;

merging the set of the sub-area images on the 3D model to form the image reading model.

3. The method of claim 2, wherein the step mapping the recorded images to each sub-area to create a set of sub-area images comprises:

iterating through each image and obtaining the positioning point with a closest capture time to a current image;

planning a virtual ray using the position coordinates of the obtained positioning point as a starting point and a corresponding field of view orientation as an extending direction, and obtaining an intersection point between the virtual ray and the 3D model;

obtaining the sub-area to which the position coordinates of current intersection point belong, and mapping the current image to the sub-area to which the position coordinates of current intersection point belong to form the set of the sub-area images.

4. The method of claim 1, wherein the method further comprises: setting the first frequency to be higher than the second frequency.

5. The method of claim 1, wherein, applying an interpolation filtering over a time sequence to supplement missing positioning points based on existing positioning points.

6. The method of claim 3, further comprises:

constructing a cross-verification set;

verifying the images in the set of the each sub-area images, and/or verifying quality of the images in each set of the sub-area images;

if an image does not belong to a current set, and/or if an image quality score of the image is below a preset value, moving the current image to the cross-verification set.

7. The method of claim 3, further comprises:

identifying and labeling an attribute for each image in each set of the sub-area images;

grouping the images with similar labels in each set of the sub-area images into one group;

generating a mapping identifier separately for each group of images with similar labels on the image reading model.

8. An electronic device, comprising a memory and a processor, wherein the memory stores a computer program that runs on the processor, and the processor executes for building an image reading model based on a capsule endoscope, wherein the method comprises:

driving the capsule endoscope to move within a working area, sequentially recording position coordinates and field of view orientations of the capsule endoscope at each positioning point at a predetermined first frequency, and driving the capsule endoscope to sequentially capture images at a predetermined second frequency and record the images;

constructing a 3D model corresponding to an outline of the working area based on the recorded position coordinates of the capsule endoscope at each location point;

mapping the recorded images onto the 3D model to create the image reading model;

wherein constructing a 3D model corresponding to the outer contour of the working area based on the recorded position coordinates of the capsule endoscope at each positioning point comprises:

obtaining all position coordinates of the capsule endoscope to form a raw point cloud data;

generating a 3D model corresponding to the outer contour of the working area after applying Gaussian filtering, voxelization, voxel shell extraction, smoothing filtering, and surface reconstruction sequentially to the raw point cloud data;

$$\Omega(p) = \begin{cases} 1, & p \text{ is on the outer contour of the working area} \\ 0, & p \text{ is inside or outside the circle of the outer contour of the working area} \end{cases}$$

Wherein the 3D model is represented by $\Omega(p)$.

\* \* \* \* \*